United States Patent [19]

Burger

[11] 4,221,971
[45] Sep. 9, 1980

[54] PROTECTIVE SHIELD DEVICE

[76] Inventor: William Burger, 48 Roland Rd., Jamestown, N.Y. 14701

[21] Appl. No.: 3,264

[22] Filed: Jan. 15, 1979

[51] Int. Cl.³ .............................................. G21F 5/04
[52] U.S. Cl. .................................... 250/505; 250/511; 250/520
[58] Field of Search ............... 250/505, 511, 512, 513, 250/520

[56] References Cited

U.S. PATENT DOCUMENTS

| | | | |
|---|---|---|---|
| 3,631,249 | 12/1971 | Friede | 250/505 |
| 3,784,818 | 1/1974 | Stoeckel | 250/363 S |
| 4,048,498 | 9/1977 | Gerbach | 250/511 |

Primary Examiner—Craig E. Church

Attorney, Agent, or Firm—Bean, Kauffman & Bean

[57] ABSTRACT

A protective shield device for mounting on an X-ray machine in the path of an X-ray beam characterized as including a first shield plate having a control aperture bounded by material opaque to X-rays, which is adapted to be disposed in alignment with the X-ray beam for limiting the size and configuration of such beam to that of the control aperture; and a second shield plate having first and second apertures, which are bounded by material opaque to X-rays and adapted to be selectively/alternately positioned in alignment with the control aperture upon relative movements of the first and second shield plates in order to selectively provide for three X-ray beam configurations varying in size and/or configuration one from another.

6 Claims, 5 Drawing Figures

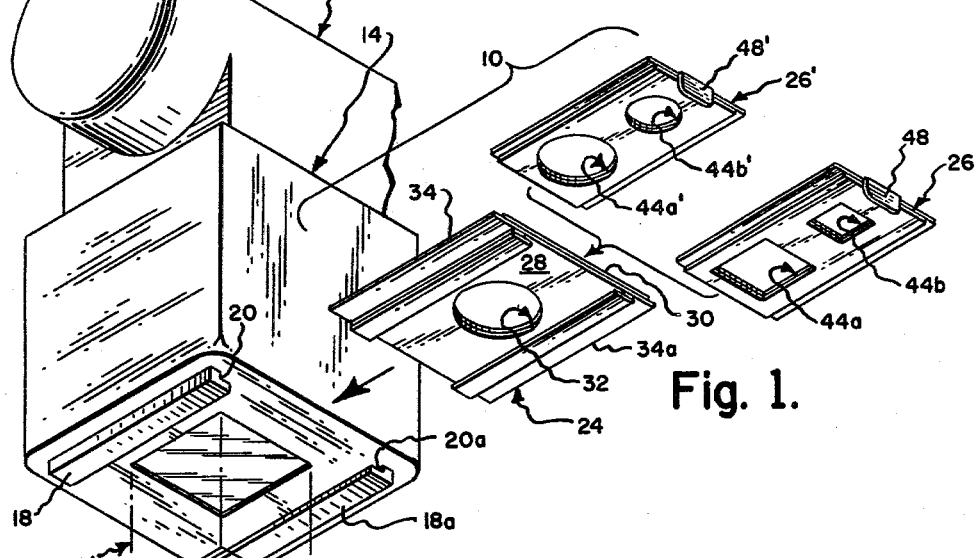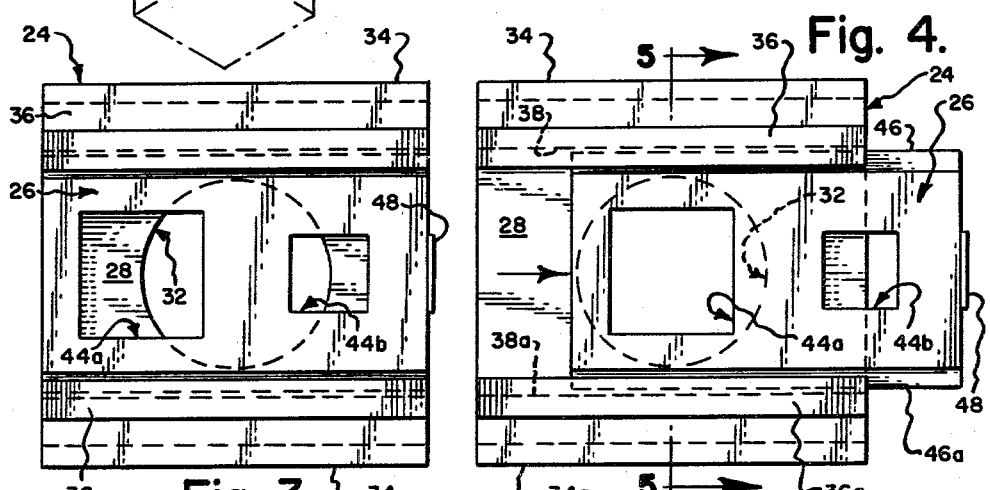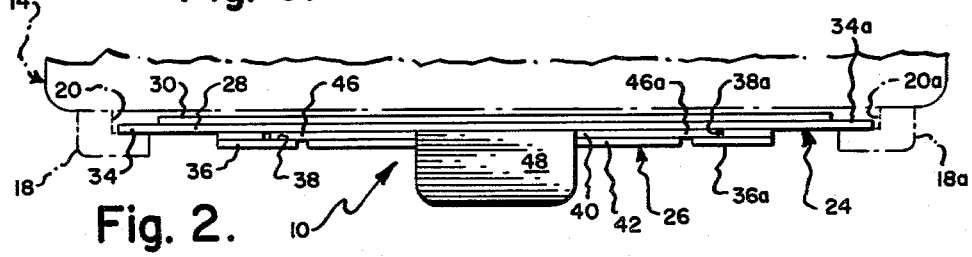

PROTECTIVE SHIELD DEVICE

BACKGROUND OF THE INVENTION

Presently available X-ray machines are commonly provided with a collimator having a continuously adjustable shutter system, which may be controlled by a technician for selectively varying the cross-sectional size of a projected X-ray beam. A practical drawback of equipment of this type is the failure of all technicians to take the time required to properly adjust the shutter system, so as to reduce beam size to that required for a given procedure and thereby minimize exposure of a subject being X-rayed to radiation.

Heretofore, various proposals have been made to fit X-ray machines with shield devices for purposes of selectively limiting the size of a projected beam size, without need for changing the adjustment or setting of the shutter system of a collimator from a most often used or preset large beam size, such as that size required for a chest X-ray procedure. One example of a shield device of this general type is that disclosed in U.S. Pat. No. 3,849,649.

SUMMARY OF THE INVENTION

The present invention is directed towards a shield device of the type adapted to be mounted on an X-ray machine to permit reduction in size of a projected X-ray beam in order to limit radiation exposure of a subject being X-rayed.

More specifically, the shield device of the present invention includes a first shield plate, which serves to define a control aperture bounded by a material opaque to X-rays and is slidably/removably supported relative to an X-ray machine in order to selectively position the control aperture in alignment with a projected X-ray beam; and a second shield plate, which serves to define first and second apertures individually bounded by a material opaque to X-rays and is slidably/removably supported relative to the first shield plate in order to selectively/alternately position the first and second apertures in alignment with the control aperture. The control, first and second apertures differ in size and/or configuration one from another whereby to permit the present shield device to selectively provide three X-ray beam configurations varying in size and/or configuration one from another.

DRAWINGS

The nature and mode of operation of the present invention will now be more fully described in the following detailed description taken with the accompanying drawings wherein:

FIG. 1 is an exploded perspective view of a shield device of the present invention in association with a conventional X-ray machine;

FIG. 2 is an end elevational view thereof;

FIGS. 3 and 4 are bottom plan views of the shield device; and

FIG. 5 is a sectional view taken generally along the line 5—5 in FIG. 4.

DETAILED DESCRIPTION

Reference is now made particularly to FIG. 1, wherein a shield device formed in accordance with the present invention is generally designated as 10 and shown in association with a conventional X-ray machine 12, including a collimator 14 depending therefrom.

As in conventional, collimator 14 includes a suitable shutter system, now shown, which is adjacent under the control of an X-ray technician for selectively varying the cross-sectional size and/or shape of a projected X-ray beam 16; and an internal light source, also not shown, which may be used to project a light beam through the shutter system in order to permit visual determination of the size or shape of the X-ray beam and/or the part of a patient's body to be exposed thereto.

Shield device 10 may be fixed to collimator 14, or directly to the X-ray machine when the latter is not provided with a collimator, in any convenient manner. However, in the preferred form of the invention, the shield device is specifically designed to be removably and slidably supported by a first pair of parallel guides 18 and 18a, which are normally provided on X-ray machines of recent manufacture for the purpose of supporting diverse equipment accessories, such as for instance X-ray beam expansion limiting cylinders and shield devices of the type disclosed for instance in U.S. Pat. No. 3,649,835. By reference to FIG. 1, it will be understood that guides 18 and 18a are arranged to straddle beam 16 and serve to define facing guide channels 20 and 20a.

Now referring particularly to FIGS. 1—3, it will be understood that shield device 10 generally includes a first shield plate 24, which is adapted to be removably slide supported within guide channels 20 and 20a; and one or more second shield plates 26 and 26', which are adapted to be selectively and removably slide supported by first shield plate 24. First shield plate 24 is preferably of a laminated construction comprising a lower mounting plate portion 28 formed of steel or other suitable material providing for a relatively strong/rigid construction and an upper shield plate portion 30 formed of lead or other suitable material impermeable or opaque to X-rays. Plate portions 28 and 30 are shown in FIG. 5 as being formed with aligned apertures cooperating to define a centrally located control aperture 32 adapted to be aligned with beam 16 when opposite side marginal edges 34 and 34a of mounting plate portion 28 are slide fitted within and centered lengthwise of channels 20 and 20a. A second pair of parallel guides 36 and 36a are suitably fixed, as by spot welding, to depend from plate portion 28 in a straddling relationship to control aperture 32 and serve to define facing guide channels 38 and 38a.

Second shield plate 26 is similar to first shield plate 24 in that it is of a laminated construction comprising an upper mounting plate portion 40 formed of steel or other suitable material providing a relatively strong/rigid construction and a lower shield plate portion 42 formed of lead or other suitable material opaque to X-rays. Further, plate portions 40 and 42 are formed with aligned apertures cooperating to define first and second apertures 44a and 44b, which are spaced apart lengthwise of plate 26 and arranged in alignment centrally thereof.

In the illustrated construction, mounting plate portion 40 has a lengthwise dimension corresponding to that of first shield plate 24 and a widthwise dimension permitting its opposite side marginal edges 46 and 46a to be slidably received within channels 38 and 38a. Further mounting plate portion 40 is provided with an upstanding tab 48, or other suitable device which may be grasped by an operator, to facilitate sliding displacements of second shield plate 26 relative to first shield plate 24.

By reference to FIGS. 3 and 4, it will be understood that first and second apertures 44a and 44b are both sized for receipt within the bounds of control aperture 32, differ in size one from another and are spaced apart through a distance permitting these apertures to be alternatively/individually positioned in alignment with the control aperture. Thus, movement of second shield plate 26 to the right, as viewed in FIG. 3, will arrange the relatively large first aperture 44a in alignment with control aperture 32 in the manner shown in FIG. 4. Conversely, movement of the second shield plate to the left, as viewed in FIG. 3, will arrange the relatively small second aperture 44b in alignment with the control aperture. Thus, by again making reference to the drawings, it will be understood that shield plate 26 may be selectively/removably adjacent by an X-ray technician to provide three primary or pre-set X-ray beam configurations, which vary in size and/or configuration one from another. A first of such projected beam configurations is defined by the size/configuration of control aperture 32 when second shield plate 26 is removed from cooperative association with first shield plate 24. Second and third projected beam configurations are defined by slide connecting the first and second shield plates with apertures 44a and 44b alternatively positioned in alignment with control aperture 32 in the manner described above.

While apertures 44a and 44b are illustrated as being of square configuration, it will be understood that these apertures may be of circular configuration, as indicated in the case of shield plate 26' in FIG. 1. Alternatively, the first and second apertures of any given second shield plate may be of different configuration. Thus, the sizes/configurations of the first and second apertures of any given second shield plate and the number of different second shield plates provided in combination with first shield plate 24 may be varied, depending on the sizes/configurations of projected X-ray beam desired for performing given X-ray procedures.

It will be noted that in the preferred form of the present invention, steel plate portion 28 comprises the lower laminate of shield plate 24 in order to facilitate slide support thereof within guides 18 and 18a and attachment of guide channels 38 and 38a. On the other hand, steel plate portion 40 comprises the upper laminate of shield plate 26 in order to facilitate slide support thereof within guide channels 38 and 38a; to permit reduction of the vertical dimension of such guide channels; and to minimize the overall weight of shield plate 26 as a result of insetting of the opposite side marginal edges of lead plate portion 42 relative to those of steel plate portion 40.

In that the spacing between guides 18 and 18a of presently available X-ray machines of different manufacture tend to vary, it is a practice in accordance with the preferred form of the invention to form plate portion 28 with an initial widthwise dimension corresponding to the maximum guide spacing expected to be encountered in present commercially available equipment. When shield 10 is intended to be sold for use with X-ray machines having less than such maximum guide spacing, it is a simple matter to trim off the side marginal edges 34 and 34a by required amounts; this trimming operation being facilitated, if desired, by providing such marginal edges with suitable indicia, not shown. In that a trimming operation is contemplated, it is preferable to form plate portion 30 with a widthwise dimension, which is less than that of plate portion 28 and preferably no greater than the contemplated minimum guide spacing in order to minimize waste of materials. While this minimum width of plate portion 30 will be sufficient to cover or block the maximum X-ray beam aperture setting for many collimators, it may be necessary in the case of some equipment for a technician to adjust such equipment to provide some intermediate beam aperture setting in order to avoid passage of portions of a projected beam externally of plate portion 30.

I claim:

1. A protective shield device for mounting externally of an x-ray machine in the path of an x-ray beam generated thereby, said shield device comprising:
a first support means fixed to depend from said machine;
a first shield plate having a control aperture bounded by material opaque to x-rays, said first shield plate being supported by said first support means to removably arrange said control aperture in alignment with said beam for limiting the size and configuration of said beam to that of said control aperture, said first shield plate having second support means depending therefrom; and
a second shield plate supported by said second support means for sliding movement, said second shield plate having first and second apertures bounded by material opaque to x-rays and spaced apart in the direction of said sliding movement for selective alternate positioning in alignment with said control aperture, said first and second apertures being sized for receipt within the bounds of said control aperture and differing one from another and when positioned within the bounds of said control aperture selectively serving to limit the size and configuration of said beam, as limited by said control aperture, to that of said first and second apertures.

2. A shield device according to claim 1, wherein said first support means defines a first pair of guides arranged in a straddling relationship to said beam; and said first shield plate is supported by said guides for sliding movement.

3. A shield device according to claim 2, wherein said first shield plate is of laminate construction including a lower mounting plate portion having opposite side marginal edges slidably supported by said guides and an upper shield portion formed of said material, said second support means is fixed to said lower mounting plate portion and defines a second pair of guides arranged to extend one along each of said opposite side marginal edges, said portions of said first shield plate being formed with aligned apertures defining said control aperture; and said second shield plate is of laminate construction including an upper mounting plate portion having opposite side marginal edges slidably supported by said second pair of guides and a lower shield portion formed of said material, and said portions of said second shield plate being formed with pairs of aligned apertures defining said first and second apertures.

4. A shield device according to claim 2 or 3, wherein said control, said first and said second apertures are of circular configuration.

5. A shield device according to claims 2 or 3, wherein said control aperture is of circular configuration and said first and second apertures are parallelograms.

6. A protective shield device intended to be mounted externally of an x-ray machine fitted with a first pair of guides arranged to depend from said machine in a straddling relationship relative to an x-ray beam generated by said machine, said shield device comprising:
- a first shield plate including a lower mounting plate portion and an upper shield portion formed of material opaque to x-rays, said portions of said first shield plate being of a laminate construction and having aligned apertures cooperating to define a control aperture, said lower mounting plate portion being sized to arrange opposite side marginal edges thereof in removable, sliding engagement with said first pair of guides for removably arranging said control aperture in alignment with said beam for limiting the size and configuration of said beam to that of said control aperture;
- support means depending from said first shield plate, said support means being fixed to depend from said lower mounting plate portion and defining a second pair of guides arranged to extend one along each of said opposite side marginal edges, and
- a second shield plate including an upper mounting plate portion and a lower shield portion formed of material opaque to x-rays, said portions of said second shield plate being of a laminate construction and having pairs of aligned apertures defining first and second apertures, said upper mounting plate portion being sized to arrange opposite side marginal edges thereof in removable, sliding engagement with said second pair of guides for removably arranging said first and second apertures alternately in a position aligned with said control aperture, and said first and second apertures being sized for receipt within the bounds of said control aperture and differing one from another and when positioned within the bounds of said control aperture selectively serving to limit the size and configuration of said beam, as limited by said control aperture, to that of said first and second apertures.

* * * * *